(12) United States Patent
Milanovich

(10) Patent No.: US 7,346,525 B1
(45) Date of Patent: Mar. 18, 2008

(54) METHOD AND SYSTEM FOR PROVIDING INSURANCE TO CONSUMERS AGAINST UNFAVORABLE OUTCOMES RESULTING FROM SERVICES, AND METHOD OF RATING RISKS ASSOCIATED WITH THE SERVICES

(76) Inventor: Philip John Milanovich, 3720 E. Kachina Dr., Phoenix, AZ (US) 85044-2515

( * ) Notice: Subject to any disclaimer, the term of this patent is extended or adjusted under 35 U.S.C. 154(b) by 507 days.

(21) Appl. No.: 10/249,270

(22) Filed: Mar. 27, 2003

(51) Int. Cl.
*G06Q 10/00* (2006.01)

(52) U.S. Cl. ............... 705/4; 705/2; 705/3; 600/300

(58) Field of Classification Search ............... 705/4
See application file for complete search history.

(56) References Cited

U.S. PATENT DOCUMENTS

| | | | |
|---|---|---|---|
| 5,655,085 A * | 8/1997 | Ryan et al. ............... 705/4 |
| 5,752,237 A | 5/1998 | Cherney |
| 5,852,808 A | 12/1998 | Cherney |
| 5,867,688 A * | 2/1999 | Simmon et al. ......... 709/208 |
| 5,999,909 A | 12/1999 | Rakshit et al. |
| 6,128,620 A | 10/2000 | Pissanos et al. |
| 6,272,471 B1 * | 8/2001 | Segal ..................... 705/4 |
| 2002/0082876 A1 | 6/2002 | Martin et al. |
| 2002/0087354 A1 | 7/2002 | Martin et al. |
| 2003/0009359 A1 | 1/2003 | Weidner et al. |
| 2003/0204415 A1 * | 10/2003 | Knowlton ............... 705/2 |
| 2004/0039689 A1 * | 2/2004 | Penney et al. ......... 705/38 |

FOREIGN PATENT DOCUMENTS

JP 2002-132955 5/2002

OTHER PUBLICATIONS www.aon.com.us/indiv/supplemental_(published on Oct. 15, 2002).*
www.camedicalmalpractice.net/faq.htm (published on Feb. 6, 2002).*
"Insurance Coverage and its cost: automobiles", by Victor Hallman et al.; Working Woman, vol. 8, p. 160, Mar. 1983.*
"New plans, new policies," by Carole King. Best's review—Life-Health Insurance Edition, vol. 86, p. 62(4), Sep. 1985; ISSN: 0005-9706. Dialog ID No. 02485505. (From Dialog File 148: Gale Group Trade & Industry DB 1976-2007/Mar. 26).*

* cited by examiner

*Primary Examiner*—C. Luke Gilligan
*Assistant Examiner*—Vivek Koppikar
(74) *Attorney, Agent, or Firm*—Stephen Christopher Swift; Swift Law Office

(57) ABSTRACT

A method of providing insurance (including professional malpractice liability insurance) to consumers against unfavorable outcomes resulting from services, and a method of rating risks associated with services. In the first preferred embodiment, a policy limit is chosen by a patient (or other consumer), a premium based on the policy limit is paid by the patient, and if malpractice is committed by a health care provider (or other professional), the patient is compensated up to the amount of the policy limit. The patient signs an agreement that the liability of the health care provider for malpractice will not exceed the policy limit. Only then are medical services provided. Risk factors are evaluated for the patient, the doctor, hospital or other health care provider, and the procedures that are to be performed, and are used to determine the amount of the premium, taking into account the policy limit chosen by the patient.

21 Claims, 10 Drawing Sheets

METHOD AND SYSTEM FOR PROVIDING INSURANCE TO CONSUMERS AGAINST UNFAVORABLE OUTCOMES RESULTING FROM SERVICES, AND METHOD OF RATING RISKS ASSOCIATED WITH THE SERVICES

BACKGROUND OF INVENTION

1. Field of the Invention

The present invention relates to insurance (including professional malpractice liability insurance) to consumers against unfavorable outcomes resulting from services, and methods of rating risks associated with the services.

2. Description of the Prior Art

The United States of America is currently facing a crisis relating to liability for medical malpractice and insurance for it. It is difficult or impossible for many physicians to pay the premiums required for adequate professional liability coverage. However, the "caps" on liability for punitive damages, that have already been enacted in some states, and are proposed in other states and at the federal level in Congress, are likely to deprive victims of adequate compensation. E.g., a young person, who is severely injured as a result of medical malpractice, may not be able to hold a normal job, and thus may be impoverished under the proposed caps, because the maximum compensation allowed under the proposed reforms may be grossly inadequate to compensate for a young person's economic losses over a lifetime. There have been a number of prior patents relating to professional malpractice and methods for reducing the cost of insurance.

U.S. Pat. No. 5,752,237, issued on May 12, 1998, to Julius Cherny, discloses a method and apparatus for providing professional liability coverage to professionals such as lawyers and accountants having large numbers of publicly traded corporate clients. It would allow the professionals or their insurance companies to sell short the stock of corporations when the price of their stock goes down due to professional malpractice. This would reduce the premiums paid by the insured professionals and/or increase the profits of the insurance companies.

U.S. Pat. No. 5,852,808, issued on Dec. 22, 1998, to Julius Cherny, discloses the same method and apparatus for providing professional liability coverage as the previous patent, but has different claims.

U.S. Pat. No. 5,999,909, issued on Dec. 7, 1999, to Amitabha Rakshit and Wilson A. Judd, discloses a method for establishing certifiable patient informed consent for a medical procedure. Like the instant invention, it uses software to reduce medical malpractice costs.

U.S. Pat. No. 6,128,620, issued on Oct. 3, 2000, to Patricia L. Pissanos and Stephen M. Beasley, discloses a database for compiling information for medical malpractice litigation.

U.S. Pat. No. 6,272,471, issued on Aug. 7, 2001, to Jeffrey J. Segal, discloses a method and apparatus for deterring frivolous professional liability claims, by paying the legal costs of countersuits for improper prosecution when a frivolous claim has been made.

U.S. Patent Application Publication No. 2002/82876, published on Jun. 27, 2002, by David A. Martin and David R. Montgomery, discloses a process for linking credentialing information with a medical malpractice insurance application.

U.S. Patent Application Publication No. 2002/87354, published on Jul. 4, 2002, by David A. Martin and David R. Montgomery, discloses the same process as the previous application, with additional claims.

U.S. Patent Application Publication No. 2003/9395, published on Jan. 9, 2003, by James Weidner, David Preimesberger and A. Peter Kezirian, Jr., discloses property/casualty insurance entities and techniques, which remove unlimited liability and cap annual assessments, while retaining the lower cost achievable by a claims-paid policy.

Japanese Patent No. 2002-132955, published on May 10, 2002, inventor Takayuki Saito, discloses a system for reducing and preventing medical malpractice.

None of the above inventions and patents, taken either singly or in combination, is seen to describe the instant invention as claimed.

SUMMARY OF INVENTION

The present invention is a method and system of providing insurance (including professional malpractice liability insurance) to consumers against unfavorable outcomes resulting from services, and methods of rating risks associated with the services. The first preferred embodiment is a method and system of providing professional liability insurance, with premiums pre-paid by consumers. A policy limit is chosen by a patient (or other consumer), a premium based on the policy limit is paid by the patient, and if malpractice is committed by a health care provider (or other professional), the patient is compensated up to the amount of the policy limit. The patient signs an agreement that the liability of the health care provider for malpractice will not exceed the policy limit. Only then are medical services provided. Risk factors are developed and evaluated for the patient, the doctor, hospital or other health care provider, and the procedures that are to be performed, and are used to determine the amount of the premium, taking into account the policy limit chosen by the patient.

The second preferred embodiment is the same as the first preferred embodiment, except that what is insured against is not only malpractice, but compensation is provided to the consumer for any unfavorable outcome of the services. The third preferred embodiment is the same as the first preferred embodiment, except that the premium is paid by the doctor or other service provider.

The fourth preferred embodiment is the same as the second preferred embodiment, except that the premium is paid by the service provider. The fifth preferred embodiment is the system of rating risks by itself, and the data bases that are created and maintained in the system, which may be used independently of the insurance system.

Accordingly, it is a first object of the invention to provide a solution to the medical malpractice insurance crisis.

It is a second object of the invention to provide an alternative system for providing medical malpractice insurance, that insures adequate compensation to injured patients, but will not bankrupt doctors or their insurance carriers.

It is a third object of the invention to provide a system of malpractice insurance that give freedom of choice to consumers.

A fourth object of the invention is to provide a system of malpractice insurance that may be adapted to any profession needing professional liability insurance.

A fifth object of the invention is to provide a system of insuring consumers against unfavorable outcomes resulting from services.

A sixth object of the invention is to provide a system for rating risks.

These and other objects of the present invention will become readily apparent upon further review of the following specification and drawings.

DETAILED DESCRIPTION

The present invention is a method for providing insurance to consumers against unfavorable outcomes resulting from services, and a method of rating risks associated with the services.

The first preferred embodiment of the invention is a system for providing professional malpractice liability insurance, in which the premiums are pre-paid by the consumers. It is designed primarily for medical malpractice liability insurance, but may also be applied to malpractice liability insurance for other professions, such as dentists, lawyers, accountants or stockbrokers.

Figure 1:
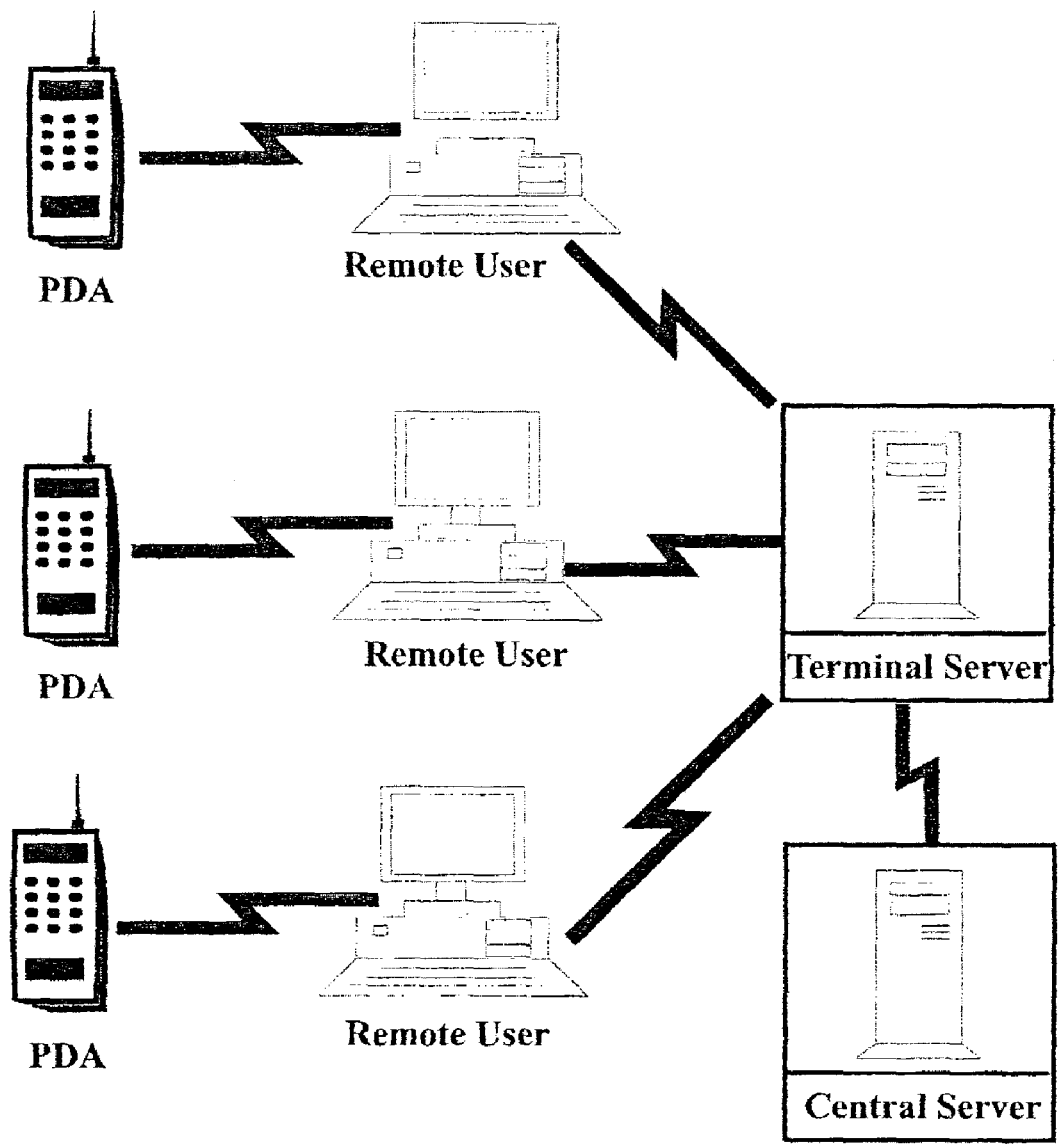
FIG. 1 is a schematic view of the secure virtual private network that may be used to implement the first preferred embodiment of the invention.

The secure virtual private network ("VPN") that may be used to implement the first preferred embodiment of the invention is shown schematically in FIG. 1. Doctors, nurses and hospital staff members may use hand held devices such as personal digital assistants ("PDAs") to link to remote user personal computers, which are linked to a terminal server, which is linked to a central server, on which are maintained the data bases used in the invention.

Figure 2:
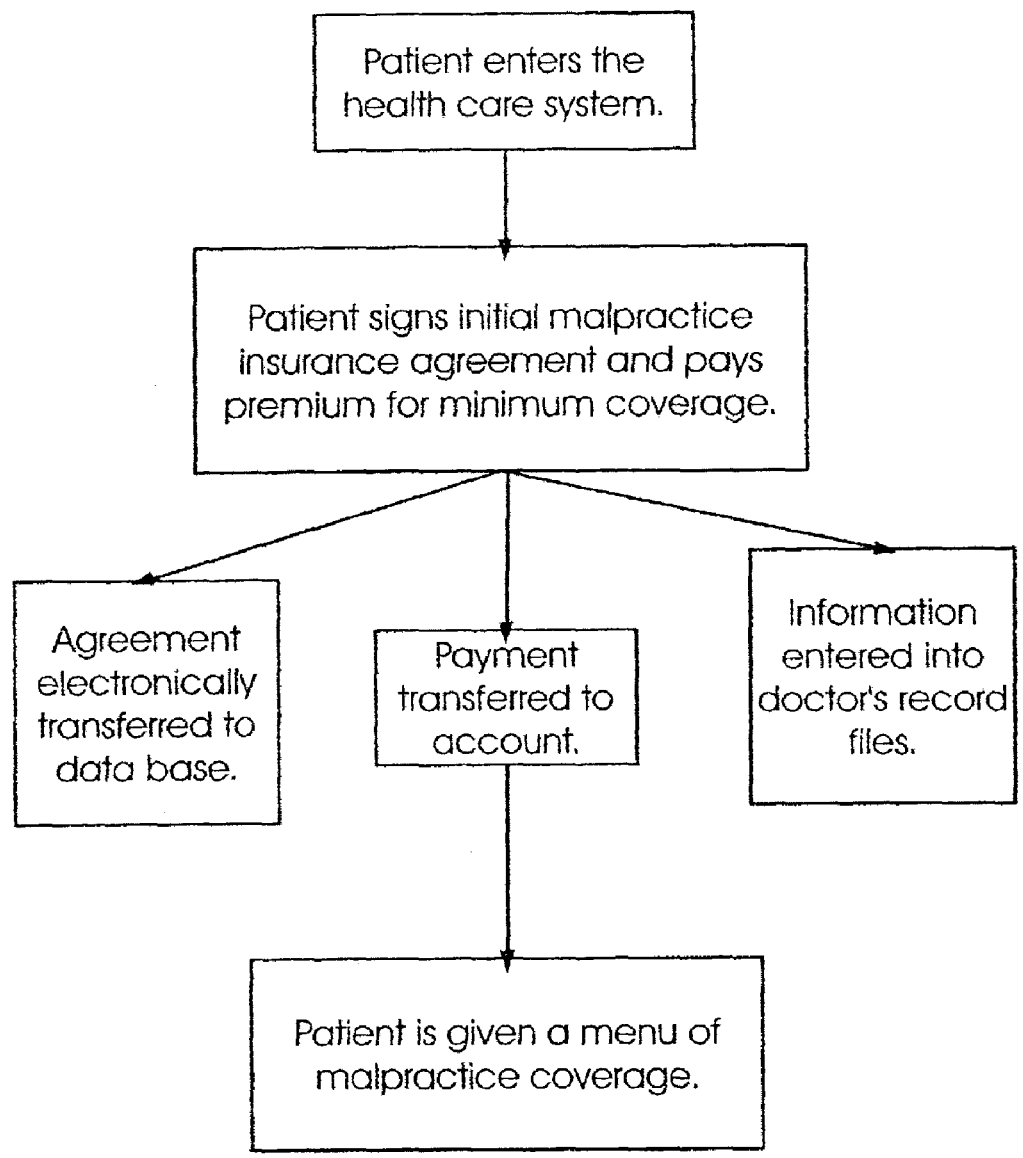
FIG. 2 is a flowchart of the initial steps in the first preferred embodiment of the invention.

The initial steps in the first preferred embodiment are summarized in the flowchart in FIG. 2. A patient (or client or other consumer) first enters the health care (or legal or other) system seeking care (or other services). (Hereinafter, only the medical application will always be discussed, but the invention may be adapted for other professions with a few obvious changes.) The consumer signs an agreement and pays a fee as a precondition to entering the system. The agreement guarantees compensation for malpractice up to a set maximum amount, called the "policy limit". The amount of the premium the consumer is willing to pay determines the maximum amount of the coverage. However, the patient is initially provided coverage only for a minimum policy limit, for a nominal fee (e.g., ten dollars) which may be considered as a processing charge. The doctor may even deduct the nominal fee from the doctor's fee for the initial office visit, so that it is a "free leader" for which no extra charge is imposed on the patient.

The agreement is electronically transferred to a data base. The consumer's payment is transferred to an account. Information is also entered into the professional's record files.

The consumer now has malpractice insurance coverage, up to the initial policy limit, before any services have been provided by the professional. The policy limit is disclosed to the consumer and agreed to by the consumer in the agreement signed by the consumer.

Figure 3:
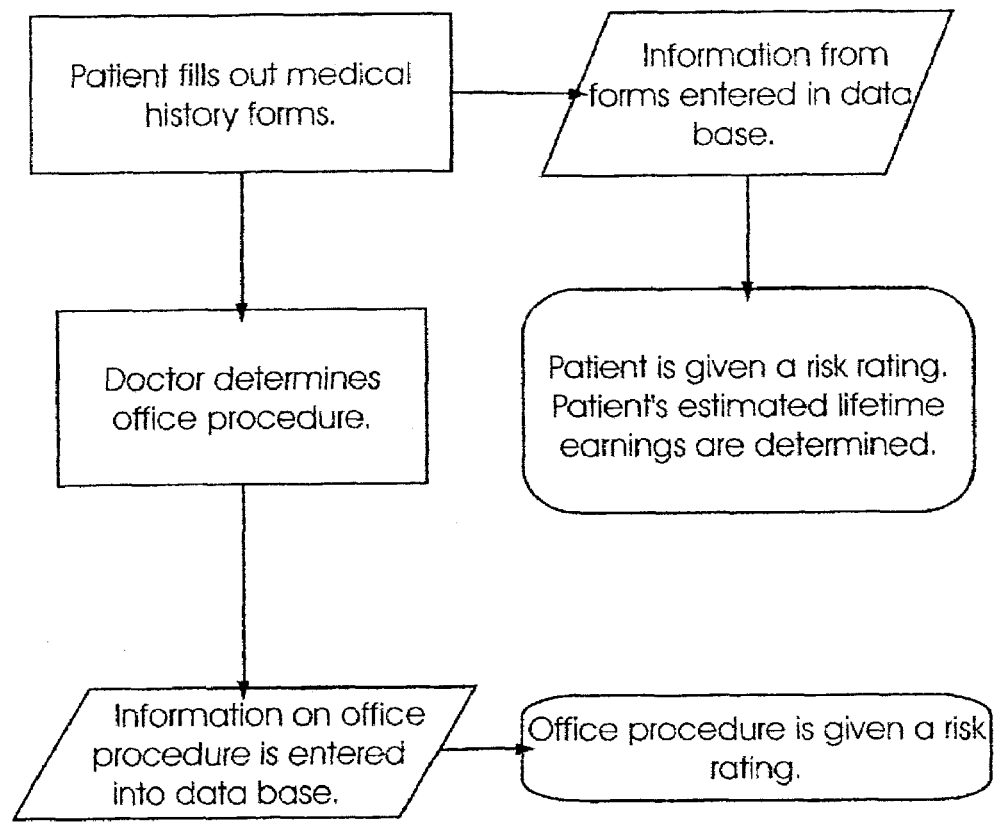
FIG. 3 is a flowchart of intermediate steps in the first preferred embodiment of the invention.

The following steps are summarized in the flowchart in FIG. 3. The patient then fills out a medical history form designed by the insurance company, as well as the doctor's medical hospital form. The forms may warn the patient that if the information provided is not true and complete, the patient will forfeit any right to compensation for malpractice. The information provided includes the patient's age, health and medical history, family history, occupation, life style, habits, work, play, and/or other objective or subjective criteria. (Other information relevant to consumer risk factors could be provided for other professions.) This information is then electronically transferred to a data base. The patient is then given a risk rating based on the information, with a certain number of points given for each negative factor (or combinations of negative factors). The patient's estimated lifetime earnings are also calculated. The doctor then determines office procedure, and that is also transferred to the data base.

The office procedure is given a risk rating. Codes for medical procedures may be taken from the American Medical Association's Current Procedural Terminology ("C.P.T." charts). Codes for diseases may be taken from the World Health Organization's International Classification of Diseases ("ICD-9" or "ICD-10" charts). A table may be developed, such as the Diagnosis Related Groups ("D.R.G."— developed by the insurance industry), with codes for medical procedures on one axis, and codes for diseases on the other axis. Each cell in the table would represent the combination of one disease with one procedure, and would be assigned a number of points based on the riskiness of the combination, with more points assigned to riskier combinations. Alternatively, procedures could be given ratings based on other objective and/or subjective criteria. (Risk ratings for services provided by other professions could be developed for those other professions.)

Figure 4:
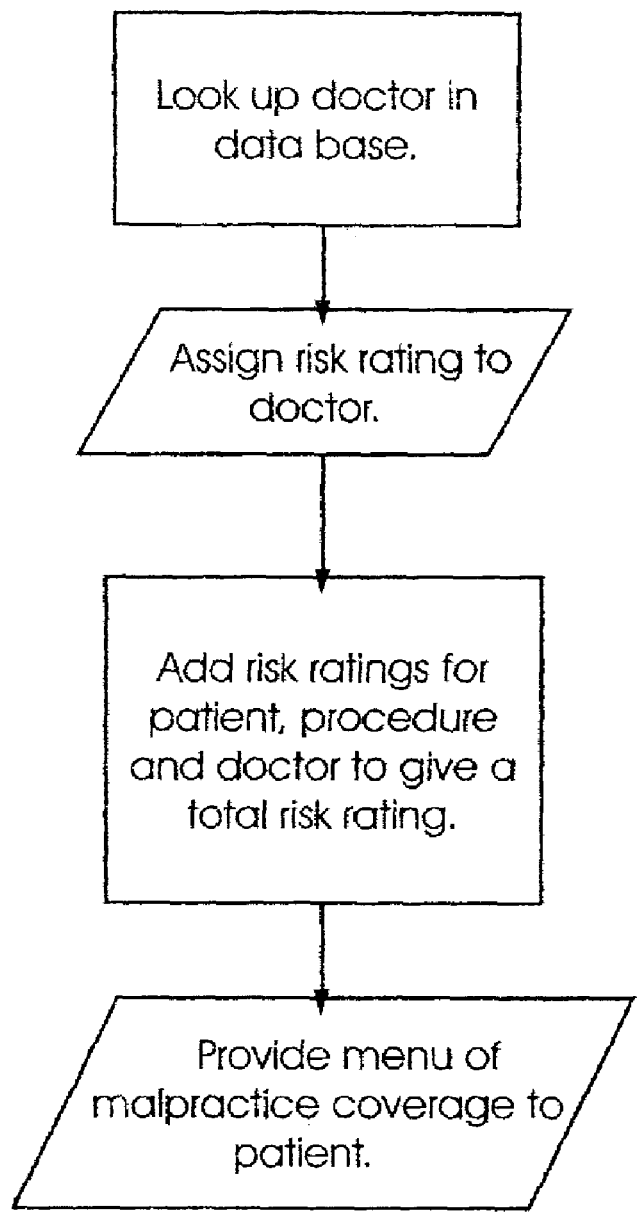
FIG. 4 is a flowchart of the final steps in the first preferred embodiment of the invention.

The following steps are summarized in the flow chart in FIG. 4. A national data base containing information on doctors is checked and the doctor is given a risk rating. The data base includes information on each doctor's field of expertise, malpractice or other complaints made against the doctor, any physical or mental disabilities that the doctor is known to have, and/or other objective or subjective criteria. The doctor would be given a certain number of points for each negative factor (or combination of negative factors). (National data bases for other professions could also be developed for those professions.) The risk rating for the patient, the doctor, and the procedure are then added to give a total risk rating. (Alternatively, they may be combined mathematically in other ways than simple addition.) The higher the total risk rating, the more costly the patient's malpractice insurance coverage will be. The patients can choose the coverage they want, ranging from basic coverage to extreme coverage. The patient is provided with a menu of malpractice coverage. They choose the coverage amount and pay the corresponding premium. For example, for illustration only:

For a policy limit of $100,000, the premium would be $25.

For a policy limit of $200,000, the premium would be $50.

For a policy limit of $300,000.00, the premium would be $75.

For a policy limit of $10,000,000, the premium would be $1,000.

A menu of insurance for lost earnings over the patient's future lifetime could be offered separately, based on the patient's estimated lifetime earnings.

Figure 5:
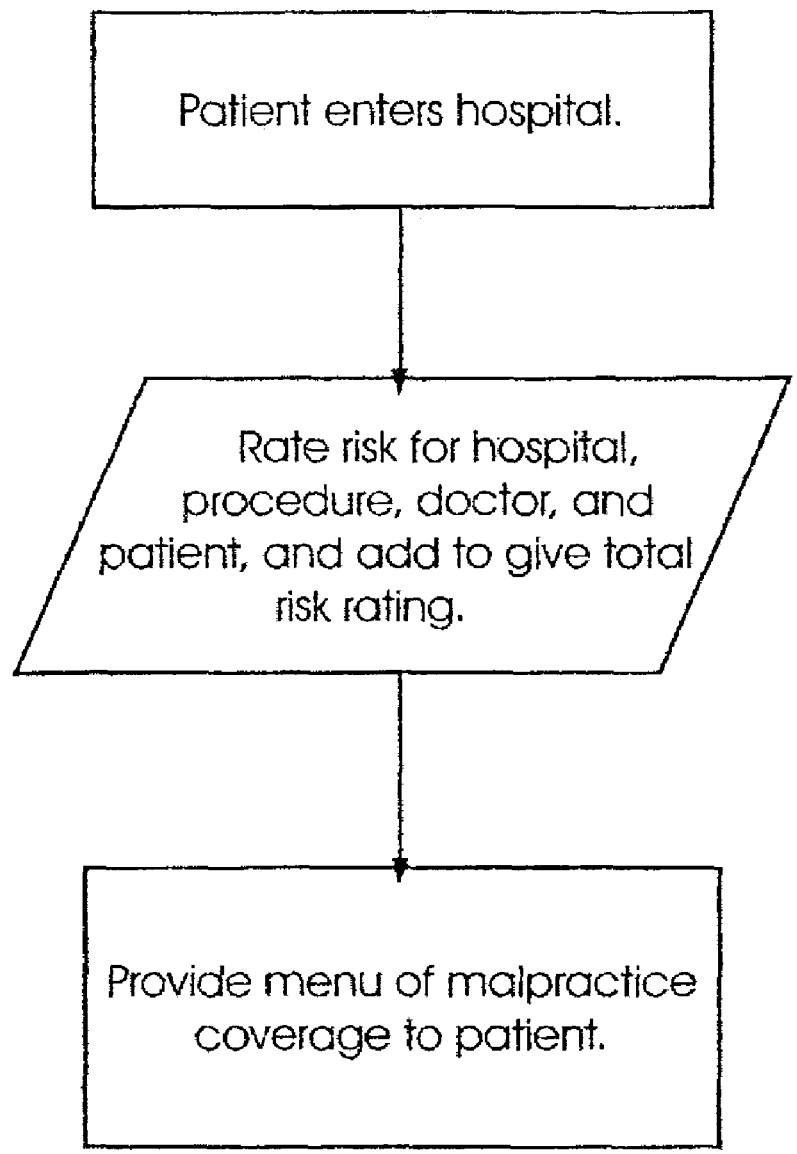
FIG. 5 is a flowchart summarizing the steps taken in the first preferred embodiment when a patient is admitted to a hospital.

The procedure followed when a patient enters a hospital (or other health care institution) is summarized in FIG. 5. If the patient enters a hospital, then the following steps are performed:

(a) The hospital's risk is rated. Factors used in determining the hospital's risk may include its size, location, the history of complaints against the hospital or against doctors at the hospital for malpractice, the ratio of nurses to beds, the ratio of specialists to beds, and/or other objective or subjective criteria. Points are given for each negative factor (or combination of factors).

(b) The risk of the procedure to be performed in the hospital is rated.

(c) The risk for each doctor or other individual health care provider involved in the procedure is rated.

(d) The patient's risk is rated.

The ratings in (a) through (d) are added together to give a total risk rating. As above, the patient is then provided with a menu of malpractice coverage, with premiums determined by the total risk rating and the policy limits chosen by the patient.

Computers will be used to calculate the risk ratings and premiums. The data bases will be maintained on computers.

Figure 6:
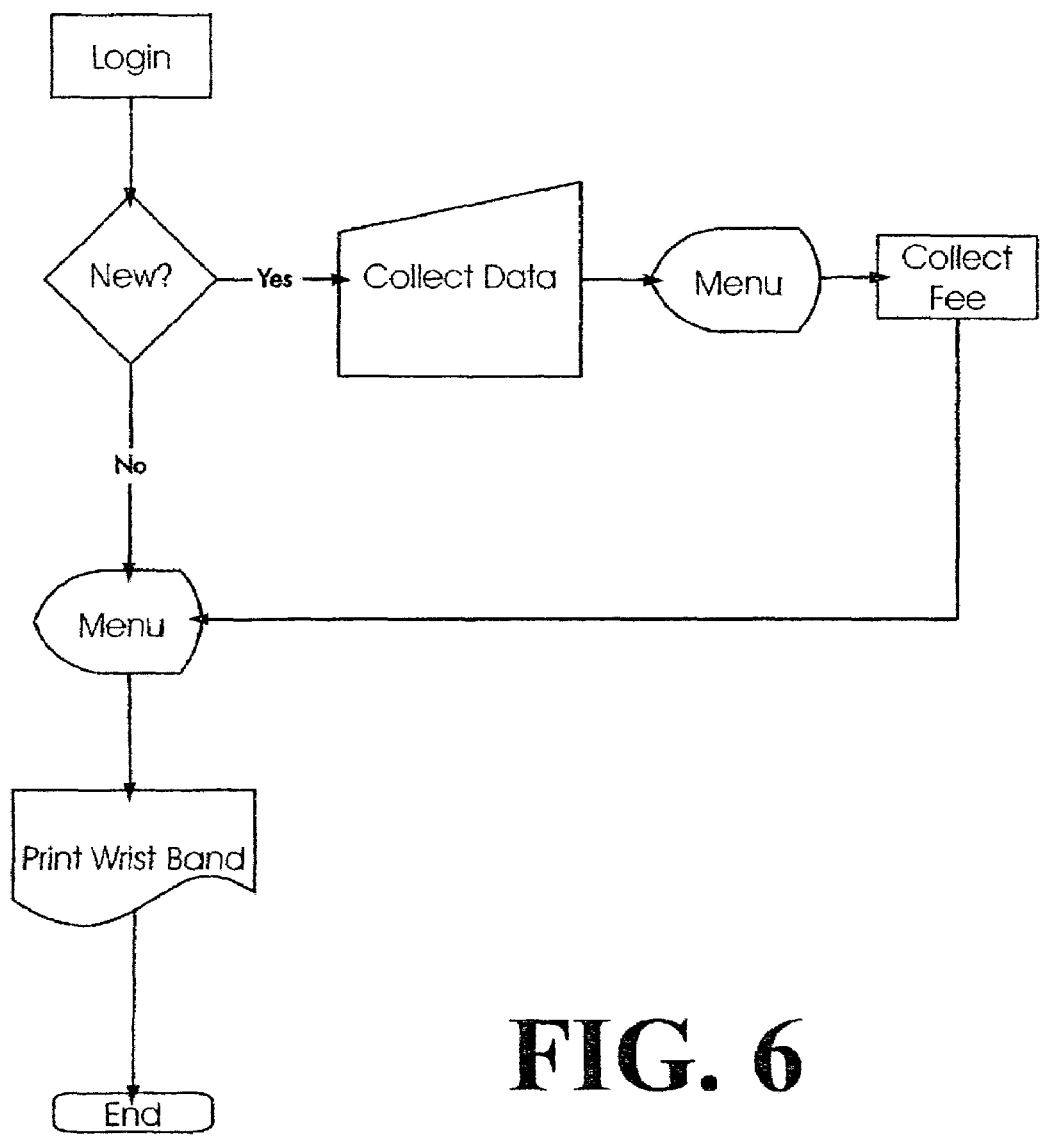
FIG. 6 is a flowchart summarizing the steps taken in patient interaction with the system of the first preferred embodiment of the invention.

The steps taken in patient interaction with the system are summarized in FIG. 6. The patient (or a staff member acting for the patient) logs into the system. If the patient is a new patient, background information and data about current medical problems of the patient are collected. The patient is then presented with a menu of malpractice coverage. A fee is collected, and the patient is presented with a second menu. If the patient is not a new patient, then the second menu is presented as soon as it is determined that the patient is not a new patient. Data are then encoded in a "smart" electronic wristband worn by the patient.

Figure 7:
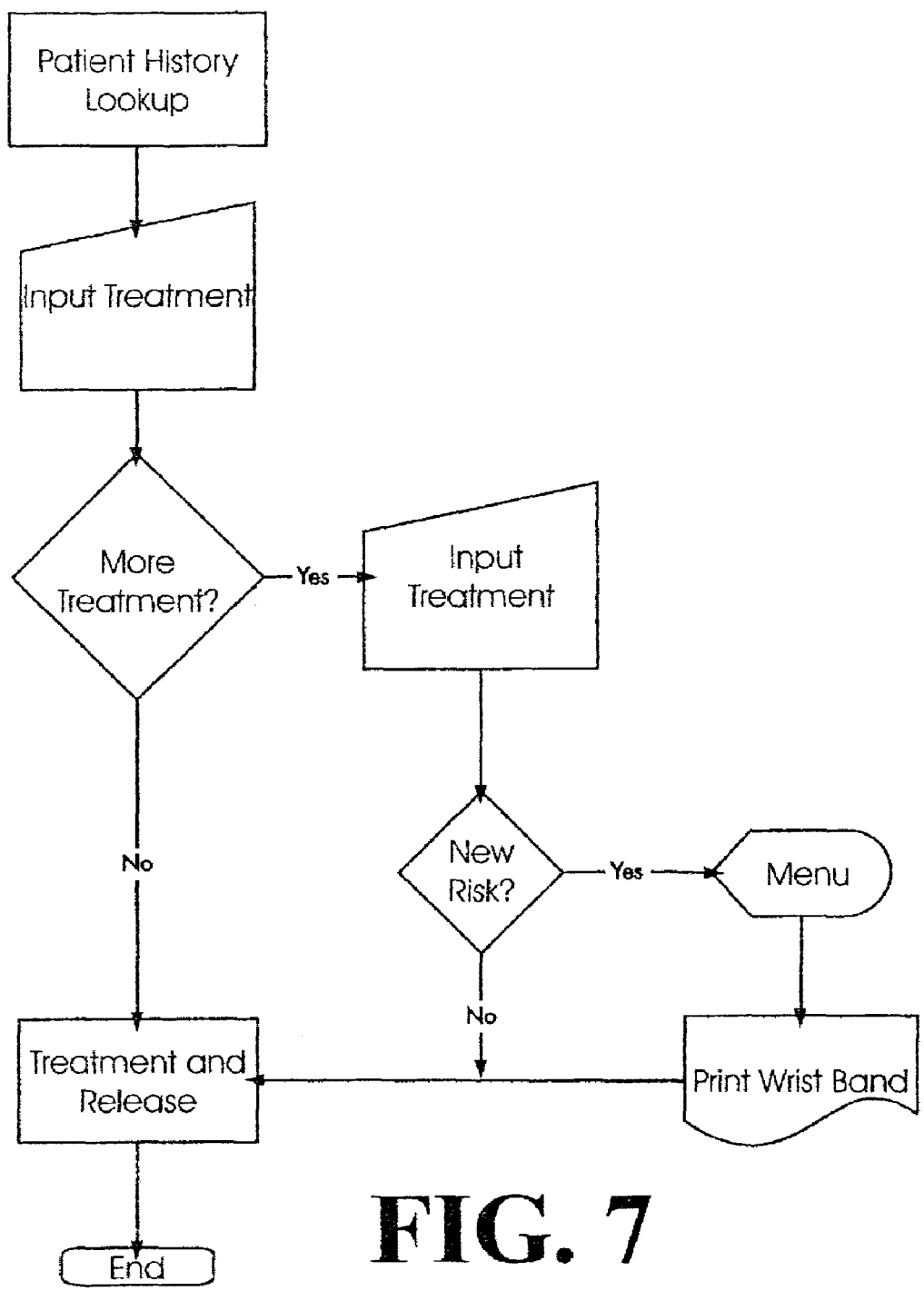
FIG. 7 is a flowchart summarizing the steps taken in doctor-patient interaction in the first preferred embodiment of the invention.

Doctor-patient interaction is summarized in FIG. 7. The doctor (or a staff member) looks up the patient's history on the computer system. The doctor inputs the treatment that has been given to the patient. If more treatments are to be given, then the doctor inputs the new treatments to be provided. If the new treatments will create new risk, the patient is then provided with a menu of malpractice coverage, data are encoded on the patient's wristband, the new treatments are then provided, and the patient is released. If the new treatments will not involve any additional risk, then the new treatments are provided without further ado, and the patient is released. If no new treatments are to be provided, then the old treatments are again given, and the patient is released.

Figure 8:
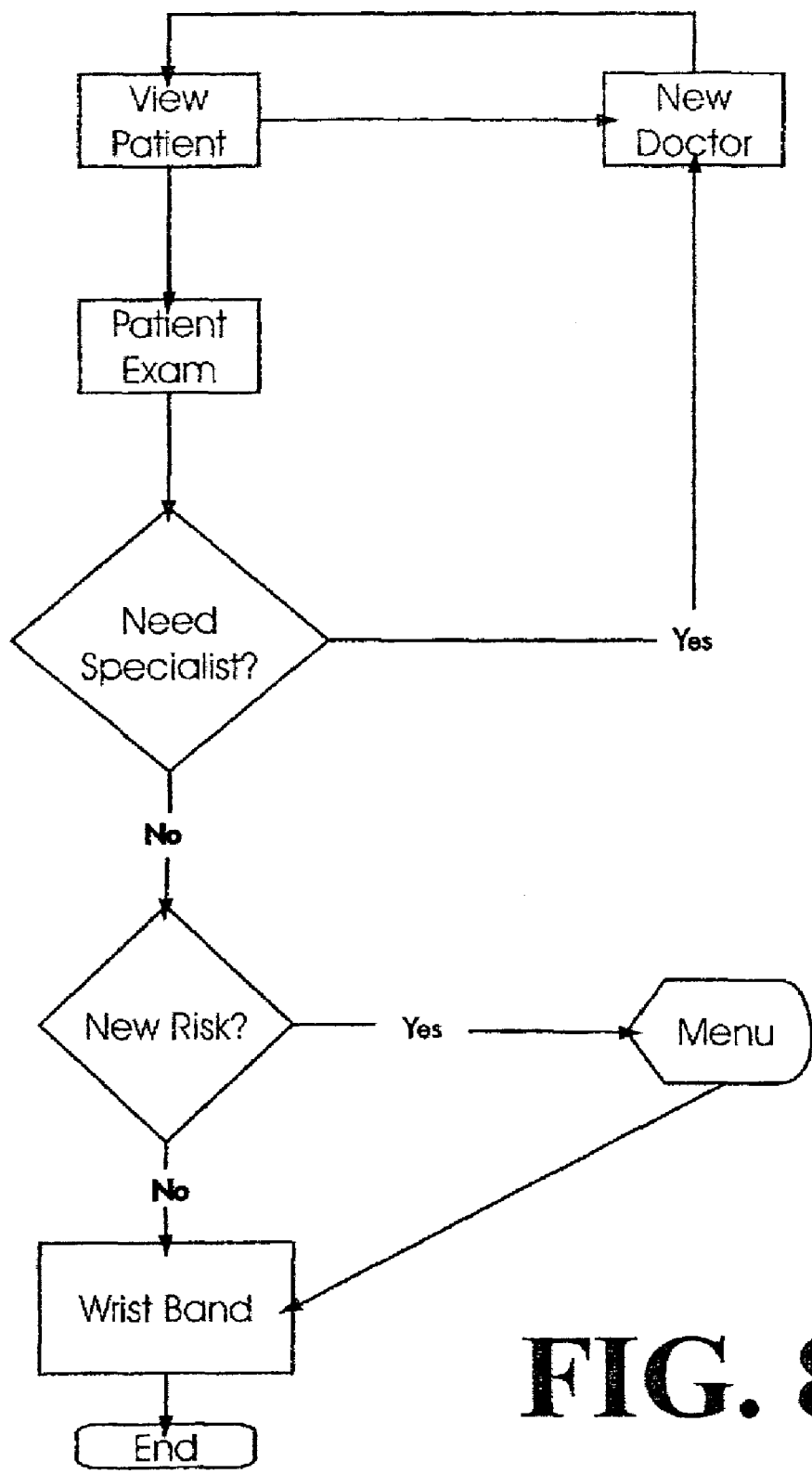
FIG. 8 is a flowchart summarizing the steps relating to a wrist band when a patient is admitted to a hospital in the first preferred embodiment of the invention.

The risk ratings may be encoded on a wrist band worn by a patient. FIG. 8 summarizes the procedure when a patient is admitted to a hospital. When a doctor first views the patient, he or she may decide to refer the patient to a new doctor right away (who will then return to the first step of viewing the patient). Otherwise, the doctor examines the patient. After the examination, the doctor may decide to refer the patient to a specialist (who will return to the first step of viewing the patient); otherwise, the doctor will determine is a new risk evaluation of the patient is necessary. After a new risk evaluation, the patient will be given a malpractice menu, as discussed above. Whether or not there is a new risk evaluation, the final step is to encode the risk factors onto a wrist band to be worn by the patient. The encoding may utilize a smart chip embedded in the wrist band, or color coding or a bar code on the wrist band.

Figure 9:
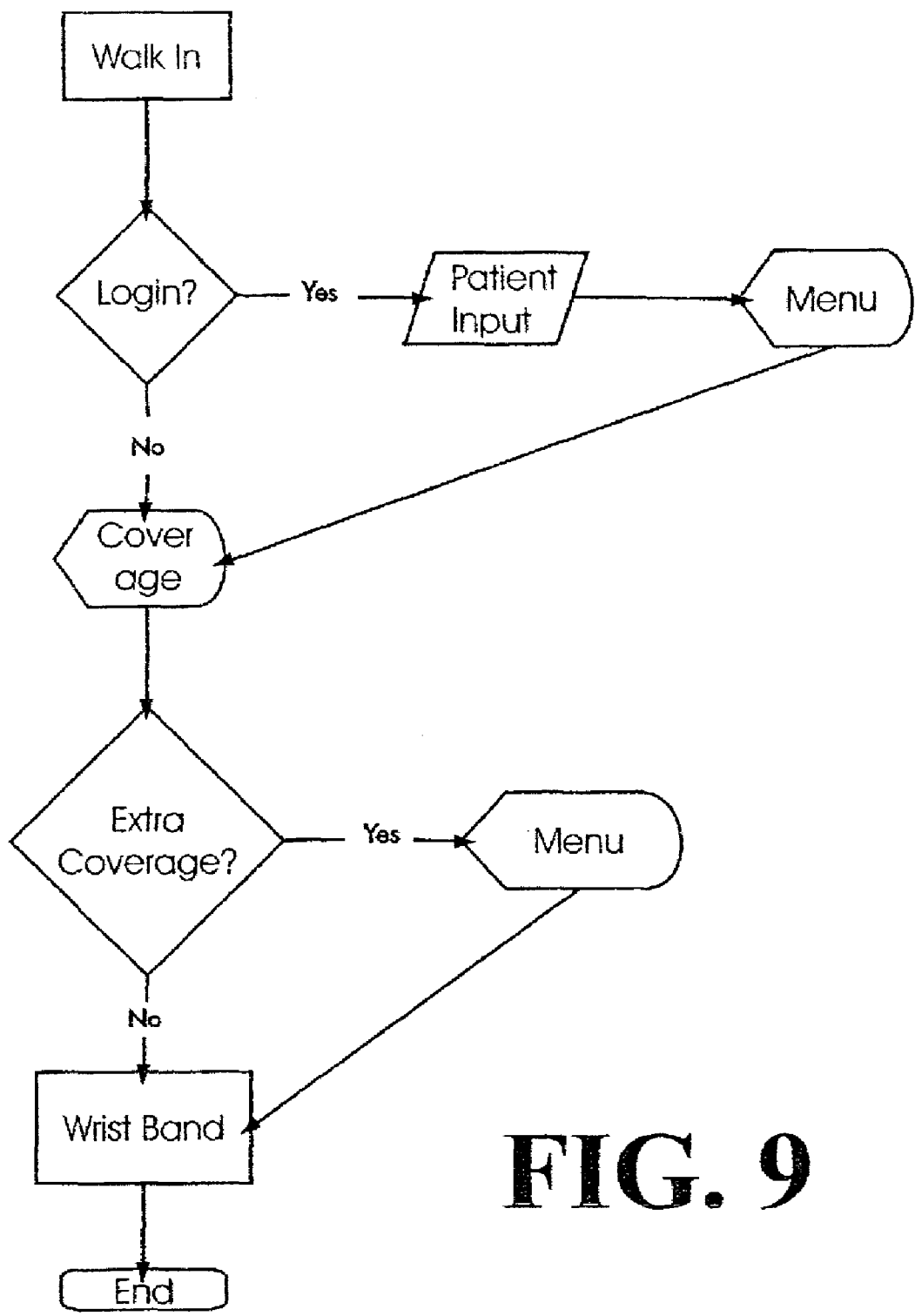
FIG. 9 is a flowchart summarizing the steps relating to a wrist band for a walk-in patient at a hospital in the first preferred embodiment of the invention.

FIG. 9 summarizes the procedure when a patient who has already been examined is admitted to the hospital on a "walk in" basis. If the patient has not already provided the necessary information, the system is logged into, information from the patient is inputted, and the patient is given a menu. The patient then selects a level of coverage. If the patient desires extra coverage, another menu is presented. Finally, the risk factors are encoded onto a wrist band.

The second preferred embodiment is the same as the first preferred embodiment, except that what is insured against is not only malpractice, but compensation is provided to the consumer for any unfavorable outcome of the services. The following are two possible examples of unfavorable outcomes that are not malpractice, for illustration only:

1. An orthopedic surgeon reconstructs a limb damaged in an automobile or industrial accident, but one of the patient's arms or legs is shorter than the other, or there is permanent scarring or other disfiguration, through no fault of the surgeon.

2. Plastic surgery makes the appearance of a patient worse, rather than better, through no fault of the plastic surgeon.

Figure 10:
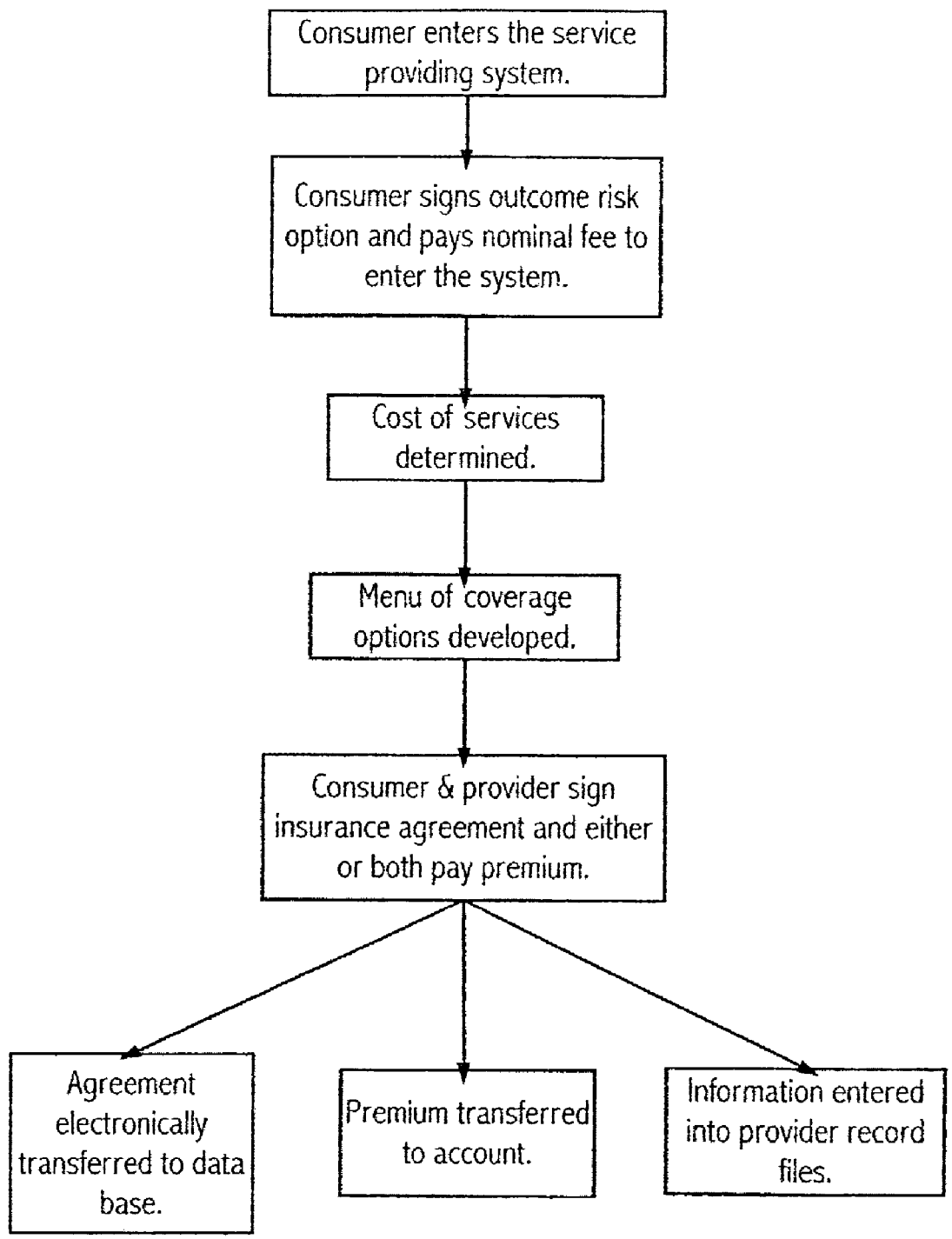
FIG. 10 is a flowchart summarizing the steps taken in the second preferred embodiment of the invention.

In such cases, the consumer would be compensated for the unfavorable outcome, even though there was no malpractice. FIG. 10 summarizes the steps taken in the second preferred embodiment of the invention. The consumer enters the (medical or other) service providing system. The consumers signs an initial agreement opting for insurance against any unfavorable outcome (which could be presented as an alternative to the malpractice insurance described above) and pays a nominal fee to enter the system. The cost of the services to be provided is determined. A menu of coverage options is developed. The consumer and the service provider then sign an agreement proving for unfavorable outcome insurance, and the consumer pays the premium. (Alternatively, the premium may be paid by the service provider or by both the consumer and the service provider.) The agreement is then electronically recorded and the record is transferred to a data base. The premium paid is transferred to an account. Relevant information is entered into the service provider's record files.

The third preferred embodiment is the same as the first preferred embodiment, except that the premium is paid by the doctor or other service provider.

The fourth preferred embodiment is the same as the second preferred embodiment, except that the premium is paid by the service provider.

The fifth preferred embodiment is the system of rating risks by itself, and the data bases that are created and maintained in the system, as described above, used independently of the insurance system.

It is to be understood that the present invention is not limited to the preferred embodiments described above, but encompasses any and all embodiments within the scope of the following claims.

The invention claimed is:

1. A method for providing medical malpractice insurance, comprising the following steps:
   (a) inputting a medical code for a particular service;
   (b) displaying a menu of policy limits and corresponding premiums for an insurance policy to be purchased by a patient prior to the particular service being provided, said menu being based at least in part on the medical code inputted;
   (c) receiving a selection from the patient of one of the policy limits and its corresponding premium;
   (d) receiving payment from the patient of the premium corresponding to the policy limit chosen the patient; and
   (e) if and only if a breach of a duty of care is committed by a health care provider, the patient is compensated only for the malpractice up to the amount of the policy limit;
   receiving from the patient an indication of agreement that the liability of the health care provider for malpractice will not exceed the policy limit.

2. The method for providing medical malpractice insurance according to claim 1, wherein the premium is paid, and the agreement to limit liability is made, before services are provided by the health care provider to the patient, and the particular service being provided is a surgical operation.

3. The method for providing medical malpractice insurance according to claim 1, wherein at least one risk factor is evaluated, and is used to determine the amount of the premium, taking into account the policy limit chosen by the patient.

4. The method for providing medical malpractice insurance according to claim 3, wherein:
   at least one risk factor associated with the patient is used to determine a patient rating that is used to determine the amount of the premium.

5. The method for providing medical malpractice insurance according to claim 3, wherein:
   at least one risk factor associated with the health care provider is used to determine a provider rating that is used to determine the amount of the premium.

6. The method for providing medical malpractice insurance according to claim 3, wherein:
   at least one risk factor associated with a health care procedure to be performed is used to determine a procedure rating that is used to determine the amount of the premium.

7. The method for providing medical malpractice insurance according to claim 3, wherein:
   at least one risk factor associated with the patient is used to determine a patient rating;
   at least one risk factors associated with the health care provider is used to determine a provider rating;
   at least one risk factor associated with a health care procedure to be performed are used to determine a procedure rating; and
   the patient rating, the provider rating, and the procedure rating are combined to produce a total rating that is used to determine the amount of the premium.

8. The method for providing medical malpractice insurance according to claim 7, wherein:
   there are a plurality of risk factors associated with the patient, including the patient's medical history, age, occupation and habits;
   there are a plurality of risk factors associated with the health care provider, including the provider's specialty and malpractice history; and
   there are a plurality of risk factors associated with the health care procedure, including both the condition being treated and the specific procedure.

9. The method for providing medical malpractice insurance according to claim 8, wherein a computer is used to calculate the premium, and the risk factors are stored in at least one data base on at least one computer.

10. The method for providing medical malpractice insurance according to claim 9, wherein information concerning the patient is stored in a device worn by the patient.

11. The method for providing medical malpractice insurance according to claim 10, wherein the device is retained on the patient by a wrist band.

12. The method for providing medical malpractice insurance according to claim 3, wherein:
    at least one risk factor associated with a health care institution is used to determine an institution rating that is used to determine the amount of the premium.

13. The method for providing medical malpractice insurance according to claim 3, wherein:
    at least one risk factor associated with the patient is used to determine a patient rating;
    at least one risk factor associated with the health care provider is used to determine a provider rating;
    at least one risk factor associated with a health care procedure to be performed is used to determine a procedure rating;
    at least one risk factor associated with a health care institution is used to determine an institution rating; and
    the patient rating, the provider rating, the procedure rating, and the institution rating are combined to produce a total rating that is used to determine the amount of the premium.

14. A method for providing professional malpractice insurance, comprising the following steps:
    (a) inputting a code for a particular service;
    (b) displaying a menu of policy limits and corresponding premiums for an insurance policy to be purchased by a consumer prior to the particular service being provided, said menu being based at least in part on the code inputted;
    (c) receiving a selection from the consumer of one of the policy limits and its corresponding premium;
    (d) receiving payment from the consumer of the premium corresponding to the policy limit chosen the consumer; and
    (e) if and only if a breach of a duty of care is committed by a professional, the consumer is compensated only for the malpractice up to the amount of the policy limit;
    receiving from the consumer an indication of agreement that the liability of the professional for malpractice will not exceed the policy limit.

15. The method for providing professional malpractice insurance according to claim 14, wherein the premium is paid, and the agreement to limit liability is made, before services are provided by the professional to the consumer.

16. The method for providing professional malpractice insurance according to claim 14, wherein at least one risk factor is evaluated, and is used to determine the amount of the premium, taking into account the policy limit chosen by the consumer.

17. The method for providing professional malpractice insurance according to claim 16, wherein:
    at least one risk factor associated with the consumer is used to determine a consumer rating that is used to determine the amount of the premium.

18. The method for providing professional malpractice insurance according to claim 16, wherein:
   at least one risk factor associated with the professional is used to determine a professional rating that is used to determine the amount of the premium.

19. The method for providing professional malpractice insurance according to claim 16, wherein:
   at least one risk factor associated with a service to be performed is used to determine a service rating that is used to determine the amount of the premium.

20. The method for providing professional malpractice insurance according to claim 16, wherein:
   at least one risk factor associated with the consumer is used to determine a consumer rating;
   at least one risk factor associated with the professional is used to determine a professional rating;
   at least one risk factor associated with a service to be performed is used to determine a service rating; and
   the consumer rating, the professional rating, and the service rating are combined to produce a total rating that is used to determine the amount of the premium.

21. The method for providing professional malpractice insurance according to claim 20, wherein a computer is used to calculate the premium, and the risk factors are stored in at least one data base on at least one computer.

* * * * *